(12) United States Patent
Shishido et al.

(10) Patent No.: US 7,399,964 B2
(45) Date of Patent: Jul. 15, 2008

(54) ELECTRON MICROSCOPE, MEASURING METHOD USING THE SAME, ELECTRON MICROSCOPE SYSTEM, AND METHOD FOR CONTROLLING THE SYSTEM

(75) Inventors: Chie Shishido, Yokohama (JP); Ryo Nakagaki, Kawasaki (JP); Mayuka Oosaki, Yokohama (JP); Hiroki Kawada, Tsuchiura (JP)

(73) Assignee: Hitachi High-Technologies Corporation, Tokyo (JP)

( * ) Notice: Subject to any disclaimer, the term of this patent is extended or adjusted under 35 U.S.C. 154(b) by 104 days.

(21) Appl. No.: 11/119,934

(22) Filed: May 3, 2005

(65) Prior Publication Data

US 2005/0247860 A1 Nov. 10, 2005

(30) Foreign Application Priority Data

May 6, 2004 (JP) ............................. 2004-137025

(51) Int. Cl.
*H01J 37/26* (2006.01)

(52) U.S. Cl. .................. 250/310; 250/311; 250/210

(58) Field of Classification Search .................. 250/310
See application file for complete search history.

(56) References Cited

U.S. PATENT DOCUMENTS 5,717,204 A * 2/1998 Meisburger et al. ......... 250/310

6,346,426 B1 * 2/2002 Toprac et al. .................. 438/8
7,095,022 B2 * 8/2006 Nakasuji et al. ............. 250/310

FOREIGN PATENT DOCUMENTS

JP 11-040096 2/1999

OTHER PUBLICATIONS

Contrast-to-Gradient Method For The Evaluation Of Image Resolution In Scanning Electron Microscopy, pp. 369-382, Japanese Society of Microscopy, Journal of Electron Microscopy, Ishitani et al, Aug. 16, 2002.
Scanning Electron Microscope pp. 48, Edited by the Japanese Society of Microscopy, Kanto Division (and Translation).

* cited by examiner

*Primary Examiner*—David A. Vanore
*Assistant Examiner*—Phillip Johnston
(74) *Attorney, Agent, or Firm*—Antonelli, Terry, Stout & Kraus, LLP.

(57) ABSTRACT

The present invention relates to an electron microscope which reduces a difference in measured values that occur due to a difference in resolution that cannot be fully adjusted which exists among electron microscopes, or occurs as time elapses, and a method for measuring dimensions. An operator adapted to compensate for changes of an electron image to be generated due to a difference in probe diameter is obtained in advance from electron images of one reference sample created by electron microscopes having different resolution (probe diameter). Then a compensation-measurement electron image which is equivalent to an electron image created under the same probe diameter by applying the operator for compensation, and the compensation-measurement electron image is used for measuring the dimensions.

10 Claims, 11 Drawing Sheets

POINT OF MAXIMUM INCLINATION AT EACH SLOPE mm

DIMENSION

FIG. 10B $th = max \times a + min \times (1-a)$ a: GIVEN RATIO (0.1 TO 1.0)

DIMENSION

FIG. 10C

SLOPE LINE
SLOPE LINE
EDGE
EDGE
BASELINE
BASELINE
DIMENSION

ELECTRON MICROSCOPE, MEASURING METHOD USING THE SAME, ELECTRON MICROSCOPE SYSTEM, AND METHOD FOR CONTROLLING THE SYSTEM

BACKGROUND OF THE INVENTION

The present invention relates to an electron microscope that is used to measure microscopic dimensions of semiconductor devices, etc., a system thereof, and a method for measuring dimensions using the electron microscope and the system.

In processes of manufacturing semiconductors, a general method employed is to measure dimensions of microscopic patterns by using electron images acquired with an SEM (Scanning Electron Microscope). Further, in general, secondary electron images, not reflected electron images, are used for measurement of the above-stated dimensions. When the term "electron image" is referred to simply as it is, it shall imply a "secondary electron image."

Figure 9A:
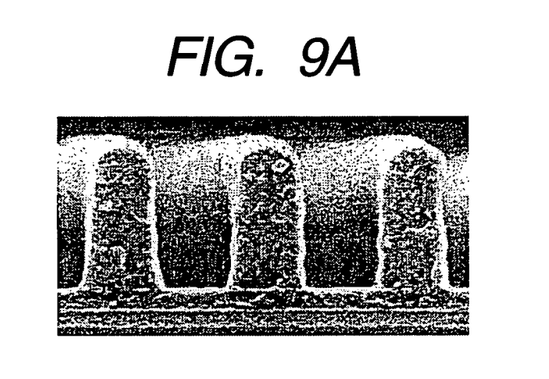
FIG. 9A shows an SEM cross-section image of an object.
Figure 9B:
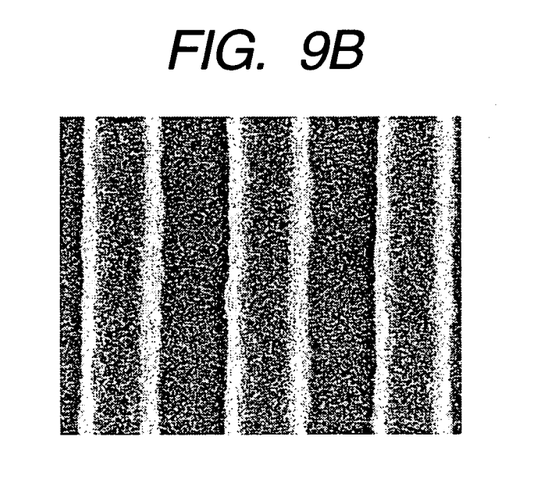
FIG. 9B shows a secondary electron image of the object.
Figure 9C:
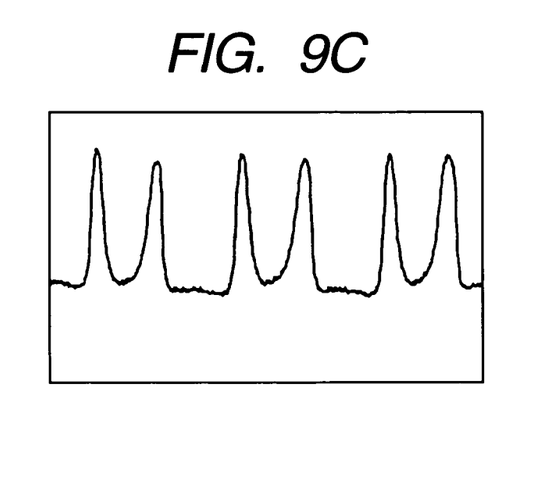
FIG. 9C shows a line profile of the secondary electron image of the object.
Figure 10A:
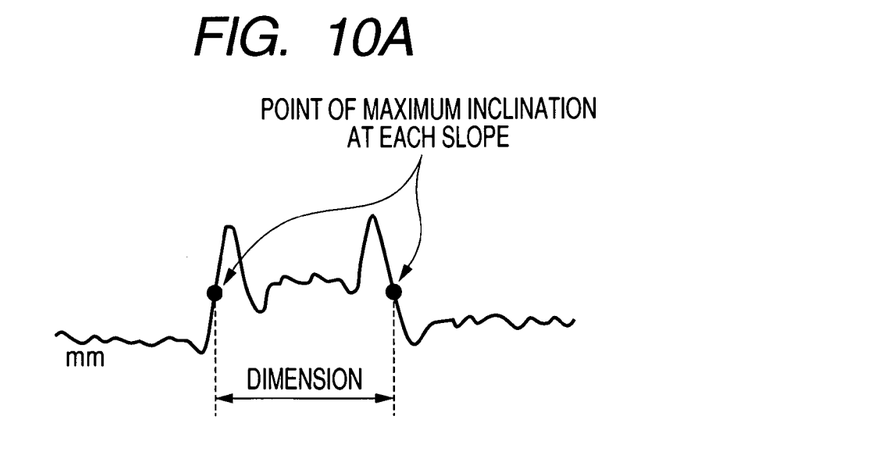
FIG. 10A is a diagram of a line profile of a secondary electron image of an object, for explaining a detection method in which the steepest gradient positions (the points of maximum inclination at slopes) are detected as edges.
Figure 10B:
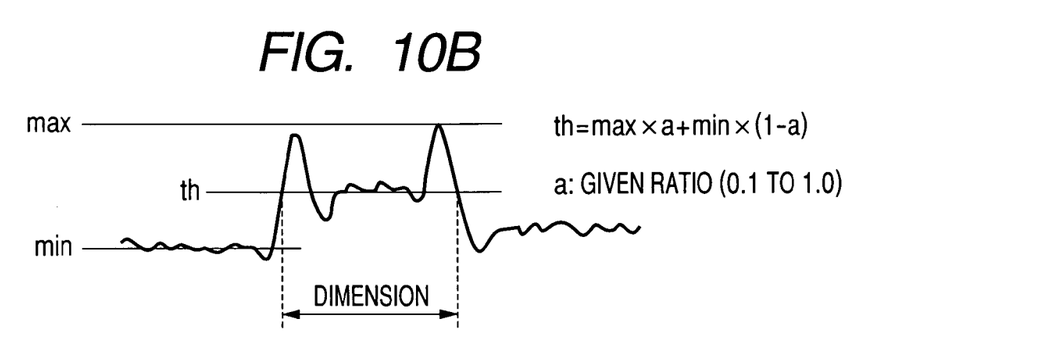
FIG. 10B is a diagram showing a line profile of a secondary electron image of an object, for explaining a method in which a given threshold value are detected as edges.
Figure 10C:
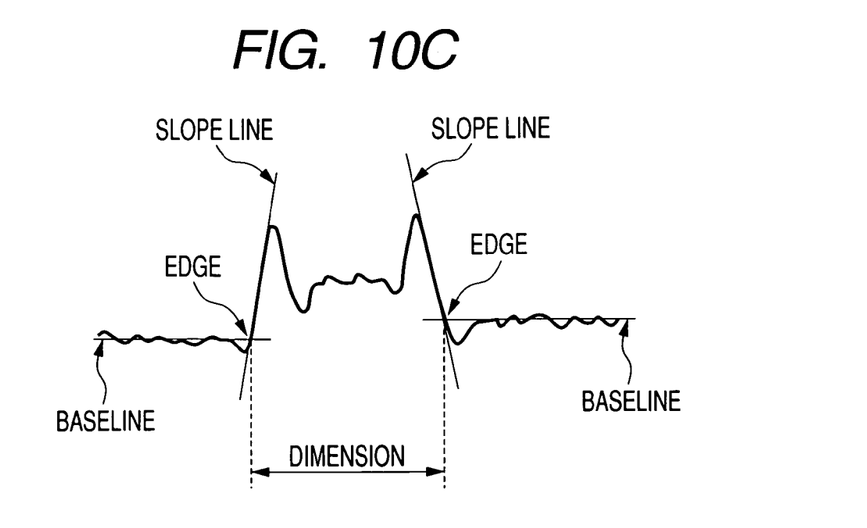
FIG. 10C is a diagram of a line profile of a secondary electron image of an object, for explaining a method in which straight slope lines are fitted to an edge portions and straight base lines are fitted to a base material portions and the intersections thus obtained are detected as edges.

Now, FIGS. 9A, 9B and 9C show the relationship among a cross-section photo of an object (FIG. 9A), a secondary electron image (FIG. 9B) and a line profile of the secondary electron image (FIG. 9C). Since the secondary electron intensity becomes larger as the slope of an object becomes larger, an image where the portions that correspond to edge areas of the object pattern become brighter and the portions corresponding to flat areas become darker as shown in FIG. 9B. For measurement of dimensions, in some cases, an image is displayed on a GUI window, and the dimension w1 (corresponding to the bottom dimension) and w2 (corresponding to the top dimension) are measured by manually moving the cursor, or alternatively, measurement of dimension is automatically conducted with various edge detection methods as shown in FIGS. 10A, 10B, and 10C. FIG. 10A shows a method for detecting the each point (the each position) of the steepest gradient (the maximum inclination at each slope) as the each edge (the steepest gradient method). FIG. 10B shows a method for detecting the each edge by using a given threshold value (th=max×a+min×(1-a), where, a: a given ratio (0.1 to 1.0)) (the threshold method). FIG. 10C shows a method wherein each straight slope line is fitted to the each edge portion and each straight base line is fitted to the each base material portion, and each intersection of these straight lines is detected as the each edge (the collinear approximation method).

Now, to convert a dimension measured on an image into an actual dimension, the scale of magnification of an SEM should be known in advance. To calibrate the scale of magnification of an SEM, a standard sample whose dimensions are known is used. As stated on page 48 of the "Scanning Electron Microscope". edited by Kanto Branch of The Japanese Society of Microscopy, the silicon microscale which is created by using anisotropic etching of silicon based on interference patterns generated by using laser beam, for example, is known as the standard sample. Since the silicon microscale carries lines and space patterns arranged in a constant pitch, and the repeated pitch thereof is determined by the wavelength of laser used, it guarantees precise values. The scale of magnification of an SEM can be determined by dividing the pitch distance on an electron image by the pitch distance of the silicon microscale.

Along with miniaturization of semiconductor device patterns, demands on measurement accuracy are becoming stricter year after year. The International Technology Roadmap for Semiconductors (ITRS) demands 0.6 nm of dimension measurement accuracy for 90 nm nodes, and 0.41 nm for 65 nm nodes. Further, the demand includes not only measurement reproducibility of a single SEM measurement apparatus, but also measurement reproducibility among electron microscope apparatuses, or more specifically, matching of measured values when an object is measured with a plurality of electron microscopes. Conventionally, to ensure consistency of measurement values among a plurality of electron microscopes, matching of scales of magnification among electron microscopes have been made by using the above-described standard sample that has known pitches.

In addition, the Japanese Patent Laid-open No. 11-40096 states an electron beam apparatus. In this apparatus, the characteristic best frequency that corresponds to the out-of-focus amount based on the Fourier spectrum of a sample image by using an out-of-focus computing unit. An out-of-focus beam distribution function corresponding to the characteristic best frequency is generated by using a beam distribution generator. The above-stated out-of-focus beam distribution function is removed from the sample image stored in a memory of one-dimensional images by using a deconvolution-computing unit. Measurement of dimensions of the sample image thus obtained is conducted with a length measurement-computing unit.

Figure 11A:
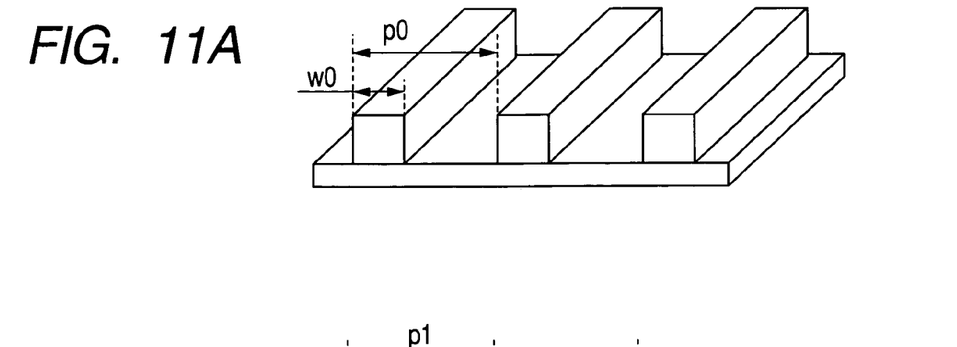
FIG. 11A is a perspective diagram of a line-and-space pattern.
Figure 11B:
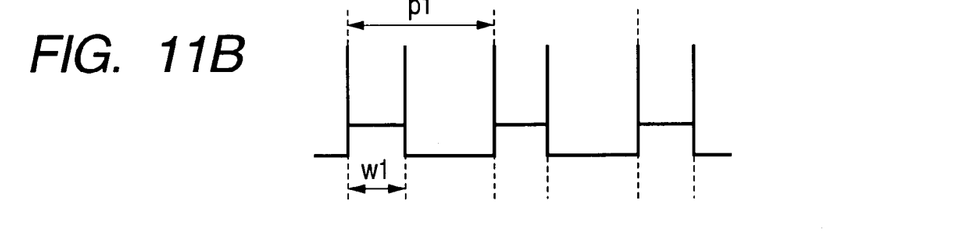
FIG. 11B is a diagram showing a line profile of a secondary electron image of the line-and-space pattern wherein the probe diameter d=0.
Figure 11C:
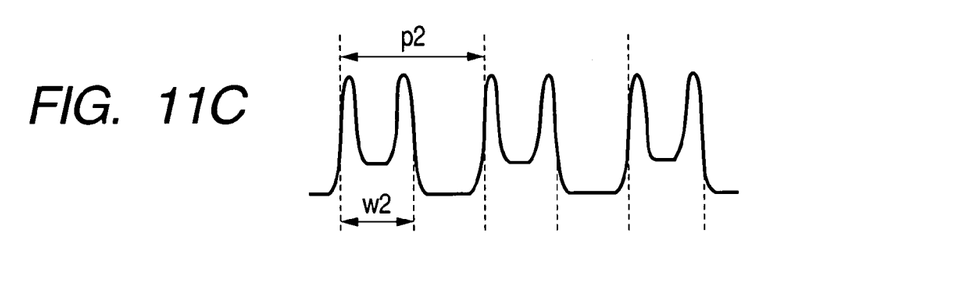
FIG. 11C is a diagram showing the line profile of the secondary electron image of the line-and-space pattern wherein the probe diameter d=d1.
Figure 11D:
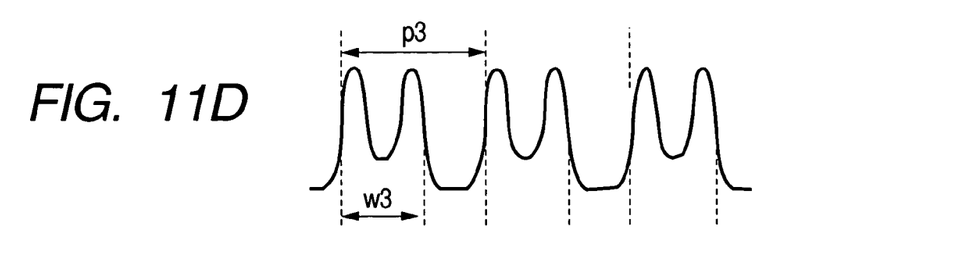
FIG. 11D is a diagram showing the line profile of the secondary electron image of the line-and-space pattern wherein the probe diameter d=d2 (>d1).

However, even if the matching of scales of magnification are made among a plurality of electron microscope apparatuses as stated above, the measurement values obtained when an object is measured may not always become matched if the resolution of the electron microscope apparatuses is different. The resolution of an SEM is dependent on the spot diameter (hereinafter referred to as the probe diameter) of the scanning primary electron beam. FIG. 11A shows a line profile of a secondary electron image having a line and space pattern (line pitch: p0, line width: w0) which has a rectangular cross section. FIG. 11B shows the line profile of the secondary electron image in the case where a probe diameter=d1=0. FIG. 11C shows the case where a probe diameter=d1. FIG. 11D shows the case where a probe diameter=d2 (>d1). The line profile based on a finite probe diameter is equivalent to the profile wherein a beam intensity distribution is convoluted on the line profile for the probe diameter 0. Therefore, the profile width which is corresponding to the pattern edge will be expanded as shown in FIGS. 11C and 11D. For example, when edge detection is conducted with the threshold method as shown in FIG. 10B, the dotted line positions on the figure are detected as edge positions.

In the above-described prior art, the matching of scales of magnification is made so that the measurement results p1, p2 and p3 of pattern pitches will conform to actual dimensions. However, as shown in FIG. 10B, the measurement result of the line width becomes larger as the probe diameter becomes larger (w1<w2<w3). As described above, even if the matching of scales of magnification are made, the measurement results of the line width will not agree in general if the probe diameters are different from each other.

Figure 1:
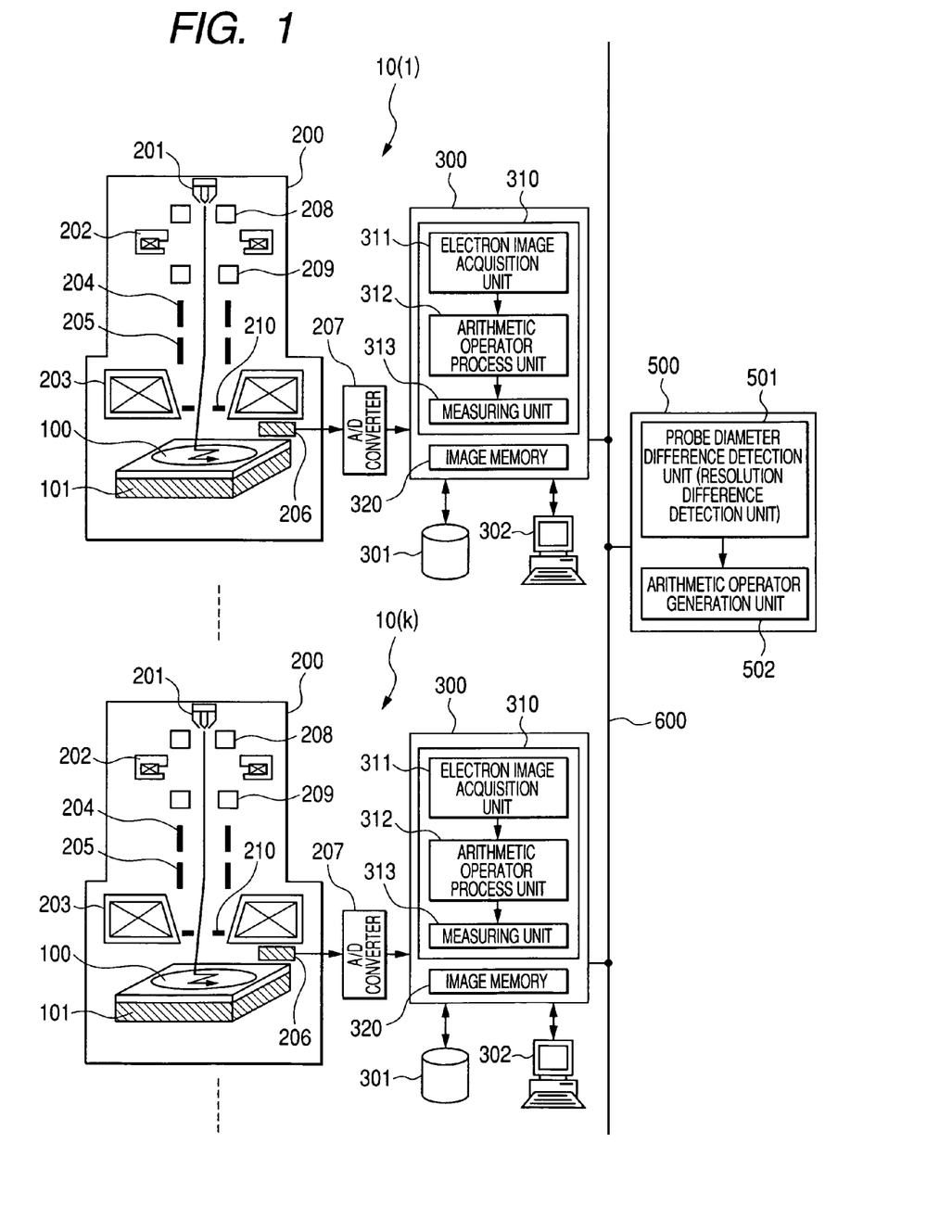
FIG. 1 is a schematic configuration diagram showing a first preferred embodiment of an electron microscope system incorporating a plurality of electron microscopes according to the present invention.
Figure 7:
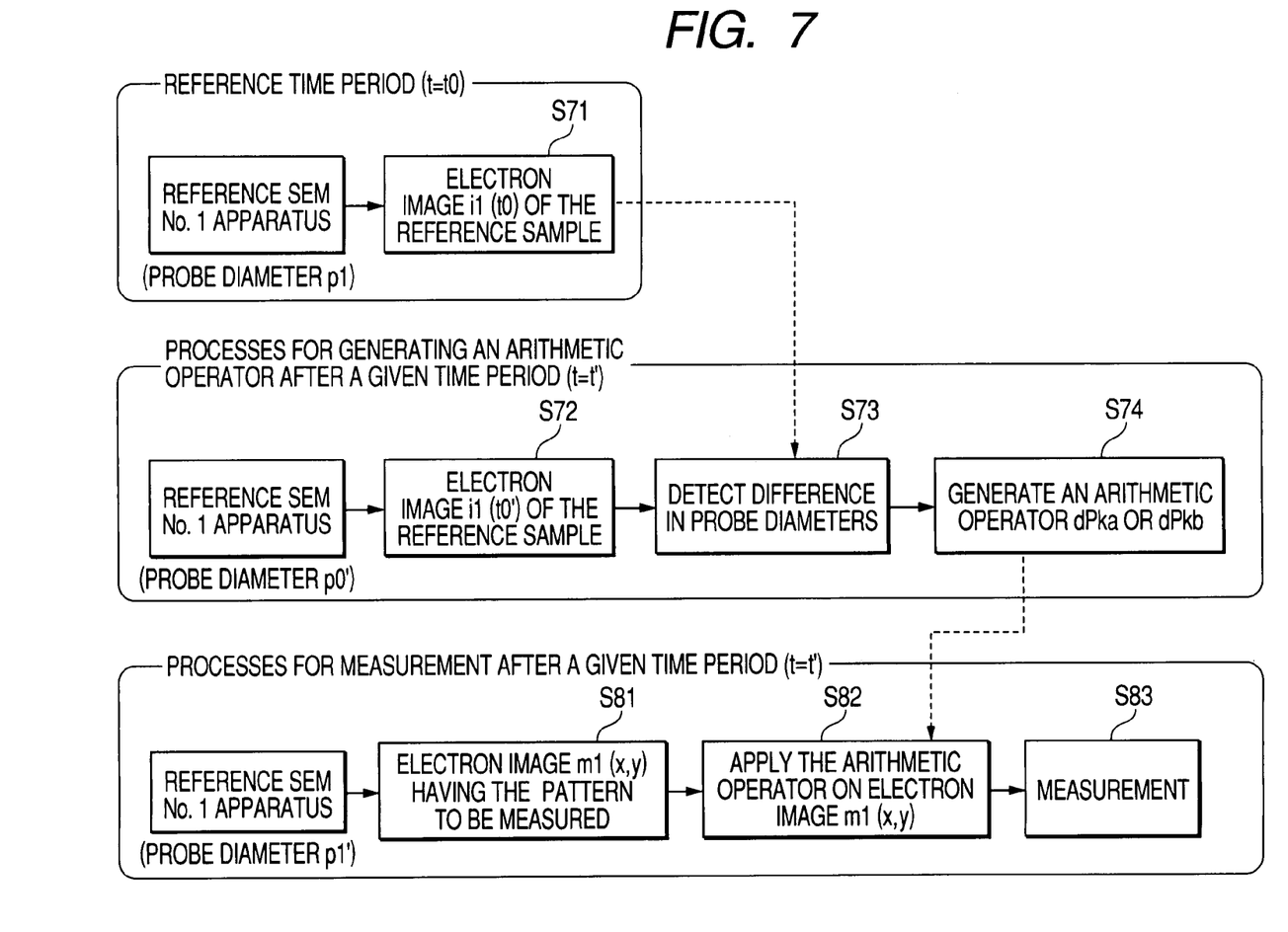
FIG. 7 is a diagram showing a flow of generating an arithmetic operator after a given time period in a main controller and a flow of measuring dimensions after a given time period in a CPU, according to the second embodiment of the electron microscope of the present invention.

The resolution of an SEM is determined by various factors such as, aberrations (spherical aberration and chromatic aberration) of an objective lens, the size of an electron source, and the aperture shape of an objective lens. It is ideal that a plurality of electron microscope apparatuses have the same resolution. However, there are individual differences among electron sources or objective lens apertures, and skills of workers who carry out optical axis alignments vary between individuals. In addition, as time elapses, deterioration of electron sources, or effects of contamination on the objective lens aperture will occur. As a result, it is practically difficult to maintain the status of matched resolution among the electron microscope apparatuses. If a difference in resolution is found, adjustment of an alignment coil (208), adjustment of an astigmatism compensation coil (209), replacement of an objective lens aperture (210), etc., which are shown in FIGS. 1 and 7, will be conducted. However, such adjustments do not always guarantee matched resolution among the electron microscopes.

SUMMARY OF THE INVENTION

The present invention provides an electron microscope which has high measuring accuracy, a system thereof, a dimension-measuring method using the electron microscope and the system, by compensating, through image data processing, a difference in resolution which exists among electron microscope apparatuses, or is generated as time elapses, and cannot be fully adjusted.

Further, the present invention facilitates retention of high measurement accuracy of the electron microscope and the system thereof by quantifying the difference in resolution stated above.

More specifically, according to the present invention, a difference in probe diameters (resolution) among electron microscopes is detected based on the reference electron image of one sample (reference sample) created with electron microscopes for reference and measurement among a plurality of electron microscopes. An arithmetic operator is generated which is adapted to compensate for the difference in probe diameters (resolution) between the reference electron microscope and the measuring electron microscope. A compensation measuring electron image is created which corresponds to the reference electron image acquired by the above-stated reference electron microscope by enabling the measuring electron microscope to make compensation, using the arithmetic operator thus generated, on a measuring electron image to be acquired from the measuring sample. Pattern dimensions are measured by using the compensation measuring electron image thus created.

According to the present invention, in an electron microscope, an arithmetic operator is generated which compensates for moment-to-moment changes in probe diameter based on the reference electron image of the electron microscope that is acquired based on a reference sample taken in a reference time period, and the reference electron image that is acquired based on a reference sample taken a given time period after the reference time period. A compensation measuring electron image is created which corresponds to the reference electron image to be acquired during the reference time period by making compensation, using the arithmetic operator thus generated, on the measuring electron image to be acquired based on the measuring sample after the elapse of the above-stated given time period. Pattern dimensions are measured by using the compensation measuring electron image thus created.

It should be noted that, for detection of a difference in probe diameter (resolution) among electron microscopes or during the period of moment-to-moment changes, two methods could be considered, for example. One is a method in which a reference electron image is Fourier-transformed, and a difference is calculated from the reciprocal (inverse Fourier transform) of the highest frequency in the power spectrum space thereof. The other is a CG method for the reference electron image (a method in which an average of edge strength over an image is defined to be the value for evaluating resolution). Further, the arithmetic operator used for compensation can be generated after all based on the difference in the probe diameter (resolution) detected.

According to the present invention, it is possible to reduce a difference in measurement values that are generated due to a difference in resolution which exists among electron microscope apparatuses, or is generated as time elapses and cannot be fully adjusted. This enables highly precise measurement.

Further, according to the present invention, it is possible to conduct monitoring of apparatus status, or adjustment work of apparatuses with a high degree of accuracy, since the above-described difference in resolution can be quantified.

These and other objects, features and advantages of the present invention will be apparent from the following more particular description of preferred embodiments of the present invention, as illustrated in the accompanying drawings.

DESCRIPTION OF THE PREFERRED EMBODIMENTS

Hereinafter, preferred embodiments of a scanning electron microscope (SEM) system comprising a plurality of SEMs and an independent SEM according to the present invention will be described.

First Embodiment

Figure 2:
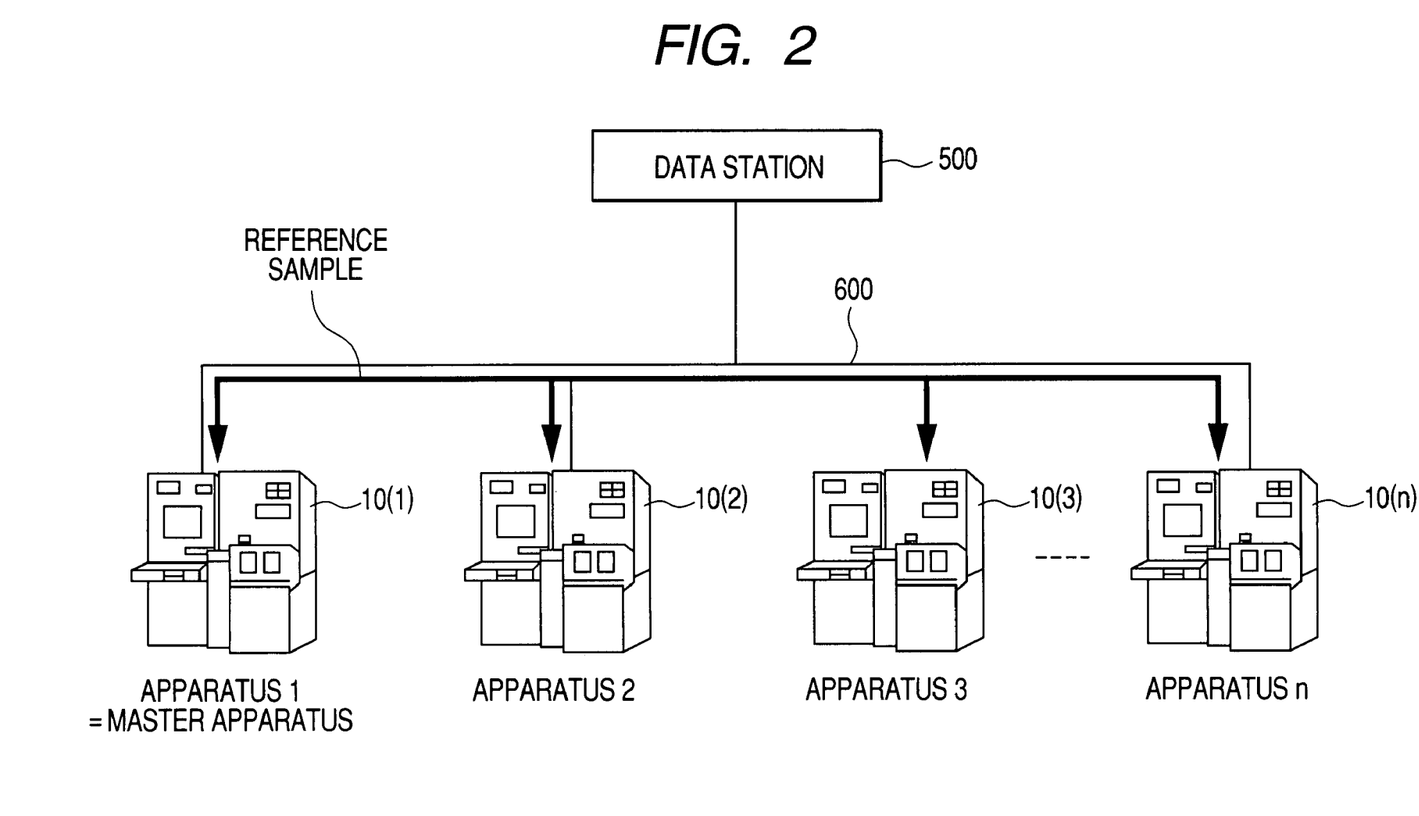
FIG. 2 is a schematic diagram of the electron microscope system shown in FIG. 1.

First, a first embodiment of the SEM system will be described with reference to FIGS. 1 to 5. FIG. 1 is a schematic configuration diagram showing the embodiment wherein SEMs (Nos. 1 to 10 apparatus) 10(1) to 10(n) are connected via a network 600, and, for example, the apparatuses are controlled by a server (data station) 500. FIG. 2 is a perspective diagram showing a schematic configuration of the embodiment. Reference numerals 10(1) to 10(3) show Nos. 1 to 3 SEMs, respectively, 10(k) No. k SEM, and 10(n) No. n SEM. Each SEM comprises a main unit (electron optical system) 200, an A/D converter 207 which converts an image signal detected by a secondary electron detector 206 into a digital image signal, an image processor 300 to which a storage device 301 and a display unit 302 are connected, and a main controller (not shown in the diagram) which controls the entire system. It should be noted that the main controller may be designed to execute part of the image processor 300. Further, the above-stated storage device 301 and the display unit 302 may be connected to the main controller.

The main unit 200 comprises: an electron gun 201; a condenser lens 202 and an objective lens 203 which focus a primary electron beam emitted from the electron gun 201 and irradiate a sample 100 with the beam as a. microscopic spot; an alignment coil 208 which aligns the primary electron beam being emitted as stated above; an astigmatism compensation coil 209 which compensates for astigmatism of the above-stated primary electron beam; deflectors 204 and 205 which scan the primary electron beam in a plane; an objective lens aperture 210; and an X-Y stage 101 which moves in an X-Y direction while carrying the sample 100 on it.

The image processor 300, to which the storage device 301 and the display unit 302 are connected, comprises a CPU 310 and an image memory 320. The CPU 310, characterizing the present invention, includes an electron image acquisition unit 311, an arithmetic operator process unit 312, and a measuring unit 313. The electron image acquisition unit 311 acquires an electron image of a reference sample pattern and a measuring target pattern of each SEM unit that are obtained through the A/D converter 207. The arithmetic operator process unit 312 acquires a resolution-compensated measuring electron image by applying (processing or calculating) an arithmetic operator dpka (x, y) or dpkb (x, y) for each SEM on an electronic image pk (x, y) of a measuring target pattern that is acquired by the electron image acquisition unit 311. The measuring unit 313 measures dimensions of microscopic patterns based on the electron image for measuring compensation that is obtained from the arithmetic operator process unit 312. The image memory 320 temporarily stores various electron images.

A server (data station) 500 that controls the SEMs 10(1) to 10(n) is functionally includes a probe diameter difference detection unit (resolution difference detection unit) 501 and an arithmetic operator generation unit 502. The probe diameter difference detection unit 501 detects difference in probe diameters (resolution difference) which is available as a difference among the SEMs based on a reference electron image il (x, y) (equivalent to the probe diameter p1) of the reference sample pattern of each SEM and a reference electron image ik (x, y) (equivalent to the probe diameter pk) of the reference sample pattern of each SEM unit. The reference electron image il (x, y) is acquired by the electron image acquisition unit 311 of the CPU 310 of the image processor 300 in the reference apparatus (master apparatus) 10(1). The reference electron image ik (x, y) is acquired by the electron image acquisition unit 311 of the CPU 310 of the image processor 300 in each SEM (e.g., No. k apparatus). The arithmetic operator generation unit 502 generates an arithmetic operator (dpka or dPkb) of each SEM (e.g., No. k apparatus) based on a difference in probe diameter detected by the probe diameter difference detection unit 501. In the above, the description has been made in which the probe diameter difference detection unit 510 and the arithmetic operator generation unit 502 are included in the server (data station) 500. However, the detection unit 510 and the generation unit 502 may be included in the image processor (including the main controller) of either of the SEMs 10(1) to 10(n) or in the image processors (including the main controllers) of all SEMs.

(1) Basic Embodiment

First, a basic embodiment according to the present invention will be described. Assuming that the reference electron image of a reference object (a reference sample) is i0 (x, y) where a probe diameter=0, the reference electron image il (x, y) where a probe diameter=p1 (x, y) can be expressed by convolution ($\otimes$) of i0 (x, y) and p1 (x, y) as shown in equation (1) below:

$$i1(x, y) = i0(x, y) \otimes p1(x, y) \quad (1)$$

Likewise, the reference electron image i2 (x, y) of the same object where probe diameter is p2 (x, y) (equivalent to that after the elapse of a given time period in No. k apparatus or No. 1 apparatus) can be expressed by convolution ($\otimes$) of i0 (x, y) and p2 (x, y) as shown in the equation (2) below:

$$i2(x, y) = i0(x, y) \otimes p2(x, y) \quad (2)$$

Here, if the probe diameter p2 (x, y) is larger than p1 (x, y), it is considered p2 (x, y) can be obtained by applying a softening filter dp (x, y) on p1 (x, y). Therefore, the following equation (3) can be derived:

$$p2(x, y) = p1(x, y) \otimes dp(x, y) \quad (3)$$

Therefore, from the relationship among equations (1) to (3), the following equation (4) can be derived between i2 (x, y) and i1 (x, y):

$$\begin{aligned} i2(x, y) &= i0(x, y) \otimes p2(x, y) \\ &= i0(x, y) \otimes p1(x, y) \otimes dp(x, y) \\ &= i1(x, y) \otimes dp(x, y) \end{aligned} \quad (4)$$

Assuming that the result of Fourier transform of i0 (x, y) is IO (X, Y) wherein capital letters indicate the result of each Fourier transform, application of Fourier transform on both sides of the above-stated equation (4) in the probe diameter difference detection unit 501, for example, provides the relationship of the following equation (5). In addition, application of inverse Fourier transform on dP (X, Y) in the arithmetic operator generation unit 502, for example, provides dp (x, y).

$$I2(X, Y)=I1(X, Y) \cdot dP(X, Y) \therefore dP(X, Y)=I2(X, Y)/I1(X, Y) \quad (5)$$

It should be noted that dP (X, Y) reflects a difference (a difference among apparatuses or moment-to-moment changes (changes with the lapse of time) in probe diameters, and, it does not depend on samples. Therefore, in the above-stated procedures, dP (X, Y) is obtained in advance, from the relationship shown in the equation (5) above, based on the ratio between a Fourier-transformed image I2 (X, Y) of the reference electron image acquired after a given time period by the electron image acquisition unit 311 of No. k or 1 apparatus and a Fourier-transformed image I1 (X, Y) of the reference electron image acquired by the electron image acquisition unit 311 of No. 1 apparatus. This makes it possible to create a compensation-measuring electron image which corresponds to the probe diameter p1 (x, y) by applying (processing or calculating) deconvolution of dP (X, Y) in the arithmetic operator process unit 312 for compensation on a measuring electron image of a different sample based on the probe diameter p2 (x, y) to be acquired in the electron image acquisition unit 311. In addition, dp (x, y) will be obtained by applying inverse Fourier transform on dP (X, Y).

As stated in the above, it is assumed that the probe diameter p2 (x, y) is larger than p1 (x, y). When the relationship is reversed, however, equation (3) above can be re-formulated to the following equation (6). As a result, the relationship of equation (7) stated below will be obtained.

$$P1(x, y)=p2(x, y) \otimes dp(x, y) \quad (6)$$

$$dP(X, Y)=I1(X, Y)/I2(X, Y) \quad (7)$$

Likewise, in this case, in the above-stated procedures, dP (X,Y) is obtained in advance, from the relationship shown in the above equation (7) above, based on the ratio between a Fourier-transformed image I1 (X,Y) of the reference electron image acquired by the electron image acquisition unit 311 of No. 1 apparatus and a Fourier-transformed image I2 (X,Y) of the reference electron image acquired after a given time period by the electron image acquisition unit 311 of No. k apparatus or No. 1 apparatus. This makes it possible to create a compensation-measuring electron image which corresponds to the probe diameter p1 (x, y) by applying (processing or calculating) deconvolution of dP (X, Y) in the arithmetic operator process unit 312 for compensation on a measuring electron image of a different sample based on the probe diameter p2 (x, y) to be acquired in the electron image acquisition unit 311. In addition, dp (x, y) will be obtained by applying inverse Fourier transform on dP (X, Y).

It should be noted that, since an electron image is a very noisy image, dp (x, y) that is calculated in the above equation (5) or (7) will also be a very noisy data. Therefore, a two-dimension Gaussian filter may be fitted to the data. Alternatively, when measurement of line patterns is intended, one-dimensional processing may be conducted, instead of making two-dimension processing, by using a line-added line profile. Further alternatively, without using Fourier transform, by assigning Gaussian filters having various sizes to dp (x, y) in equation (8) or (9), a filter size that allows the right-hand side of the equation to be closest to the left-hand side may be obtained. Also in this case, one-dimensional processing may be performed, instead of making two-dimension processing, by using a line-added line profile.

$$i1(x, y)=i2(x, y) \otimes dp(x, y) \quad (8)$$

$$i2(x, y)=i1(x, y) \otimes dp(x, y) \quad (9)$$

Namely, $\otimes$ is the convolution.

(2) Method for Detecting Difference in Probe Diameters

Next, a method for detecting a difference in probe diameters will be described. Since there is no means to directly measure a probe diameter (resolution), there is no other choice but to detect a difference in probe diameters according to a difference in electron images. A method that has been conventionally practiced is to measure the smallest gap size that is visible on an electron image by using a sample evaporated with particles of gold, etc. In this method, as the gap size will become smaller, the resolution will become higher (=smaller probe diameter). Since the method has problems in that definition on spacing of particles is unclear, and subjectivity of a measuring person is unavoidable, etc., some methods for quantifying resolution through image processing have been proposed.

The proposed methods include, for example, a method for Fourier-transforming an electron image based on the above equation (5) or (7) and calculating a difference in probe diameters from the reciprocal of the highest frequency of the power spectrum space thereof (in which data exists in a higher space frequency range as resolution becomes higher), or the CG method which is stated in Journal of Electron Microscopy 51(6): 369-382(2002).

Figure 4A:
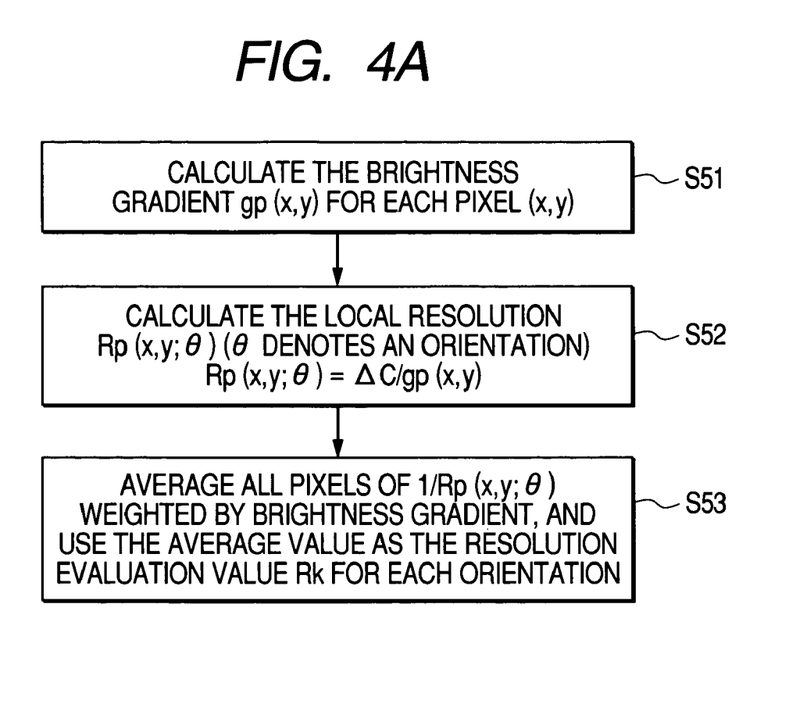
FIG. 4A is a flow diagram for explaining the sequence of processes of the CG method.
Figure 4B:
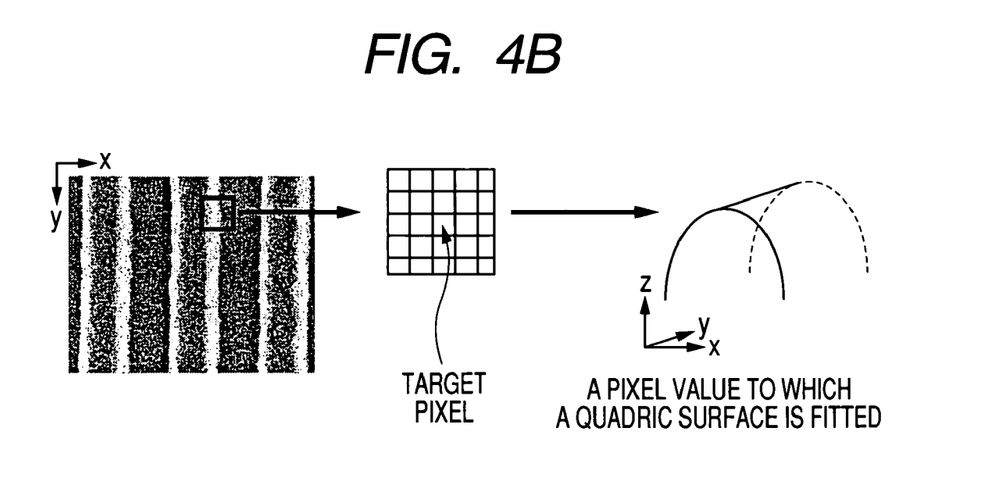
FIG. 4B is a diagram showing a flow of fitting a quadric surface to a pixel value in the kernel.

The CG method is based on a concept that resolution becomes higher as the edge strength becomes larger, and average edge strength on the overall image is used to determine an evaluation value of resolution. FIG. 4 shows the processing steps. First, a quadric surface is fit to a pixel value in a kernel (e.g., 5×5) (See FIG. 4B.), and a brightness gradient (a gray-scale gradient) gp (x, y) in each pixel (x, y) in each orientation is obtained from the quadric surface equation (S51). Next, a local resolution (resolution on each point on the image) Rp (x, y; θ) is defined as a value obtained by dividing ΔC which corresponds to the range of image brightness by the brightness gradient gp (x, y) in each orientation (S52). Then, averaging of 1/Rp (x, y; θ) is executed on all pixels, being weighted with the brightness gradient, and a resolution evaluation value $R_k$ is calculated for each orientation k (S53). The CG method has advantages of:

(a) enabling reduction in impacts of noise and calculation of resolution per orientation by fitting the quadric surface to local areas;
(b) reducing impacts of density (brightness) changes with introduction of threshold value of contrast which links to density; and
(c) reducing impacts of non-edge areas by using brightness gradient as a weighting factor.

It needs only to apply either of the methods stated above to detection of a difference in probe diameter in the probe diameter detection unit 501 to be described in the following embodiment.

(3) Operations of the First Embodiment

Figure 3:
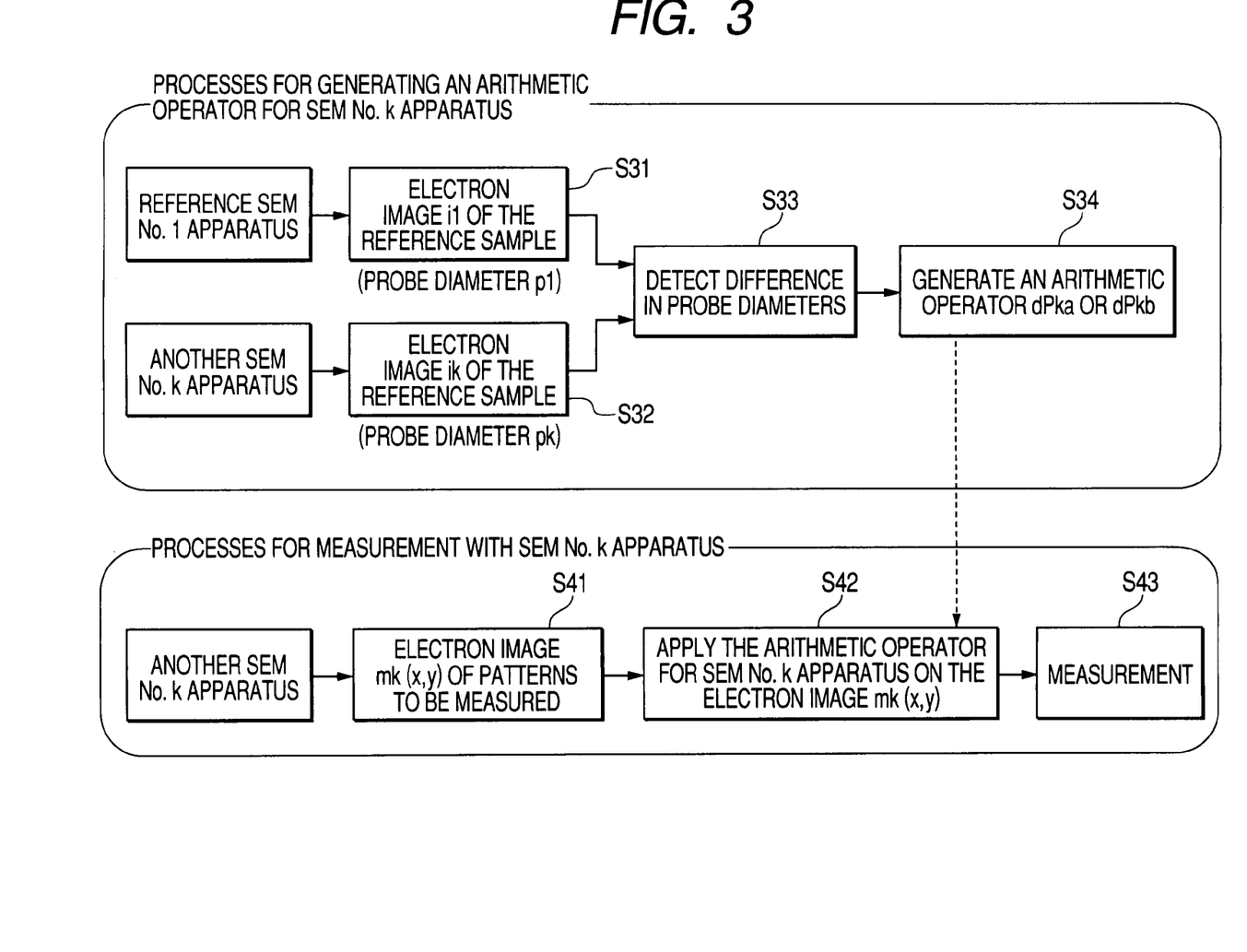
FIG. 3 is a diagram showing a flow of generating an arithmetic operator for the SEM No. k apparatus in a server (data station) and a flow of measuring dimensions in the CPU of the SEM No. k apparatus, in the first embodiment of the electron microscope according to the present invention.

A case of the first embodiment wherein an electron image corresponding to the probe diameter of the reference apparatus or No. 1 apparatus is created from an electron image mk (x, y) of the No. k apparatus 10(k) will be described with reference to FIGS. 1 to 3. The flow of processes is similar to those described in the "Basic Embodiment" stated above. The following processes will be executed in advance, using the reference sample, as shown in processes for generating an arithmetic operator for No. k apparatus, the processes comprising the steps of: acquiring an reference electron image i1

(x, y) (equivalent to the probe diameter p1) of the reference sample by using the electron image acquisition unit of No. 1 apparatus (S31); acquiring a reference electron image ik (x, y) (equivalent to the probe diameter pk) of the reference sample by using the electron image acquisition unit 311 of No. k apparatus (S32); checking a difference in probe diameters of electron images according to the "Method for Detecting Difference in Probe Diameters" stated above in the probe diameter difference detection unit 501 (S33); calculating the arithmetic operator dPka in the arithmetic operator generation unit 502 according to the above equation (5) if the probe diameter of No. k apparatus is larger than the probe diameter of No. 1 apparatus; and calculating the arithmetic operator dPkb in the arithmetic operator generation unit 502 according to the above equation (5) if the probe diameter of No. 1 apparatus is larger than the probe diameter of No. k apparatus, and storing the arithmetic operator dPkb in the storage device 301 of No. k apparatus (S34).

When actual patterns are measured in No. k apparatus 10(k), the processes comprise the steps of: in the arithmetic operator process unit 312, creating a compensation-measuring electron image which corresponds to the probe diameter of the reference apparatus or No. 1 apparatus by acquiring an measuring electron image mk (x, y) of No. k apparatus by using the electron image acquisition unit 311, and compensating the measuring electron image mk (x, y) of No. k apparatus thus acquired by applying deconvolution of the arithmetic operator dPka or dPkab which are already stored in the storage device 301 of No. k apparatus (S42); and measuring patterns in the measuring unit 313 by using the compensation-measuring electron image thus created (S43).

Figure 5:
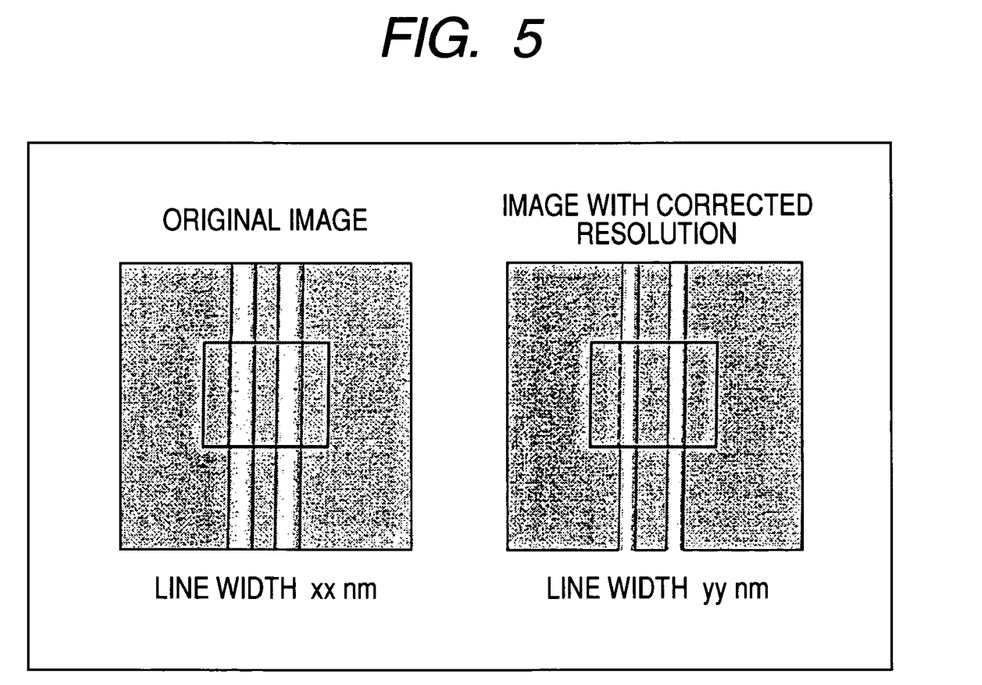
FIG. 5 is a diagram showing an embodiment of a GUI window displayed on a display unit of a given electron microscope.

FIG. 5 is a diagram showing an embodiment of a GUI window displayed on the display unit 302 of No. k apparatus. On the window, an original image, an image created (resolution-compensated image), and measurement results of respective images will be displayed. According to the embodiment, it is possible to reduce a difference (apparatus difference) in measured values among the apparatuses, thus enabling to achieve measurement accuracy required by semiconductor processes.

Second Embodiment

Figure 6:
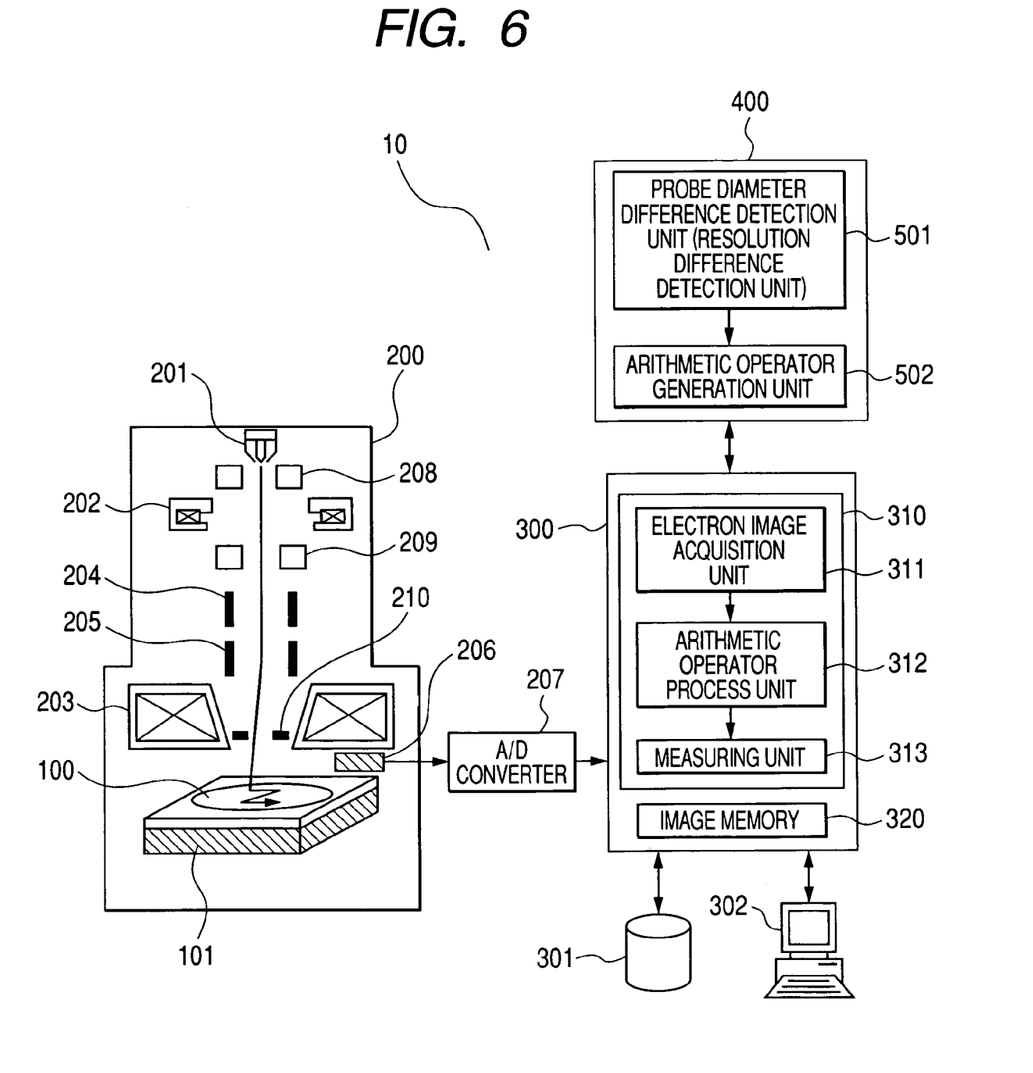
FIG. 6 is a schematic configuration diagram showing a second preferred embodiment of an electron microscope according to the present invention.
Figure 8:
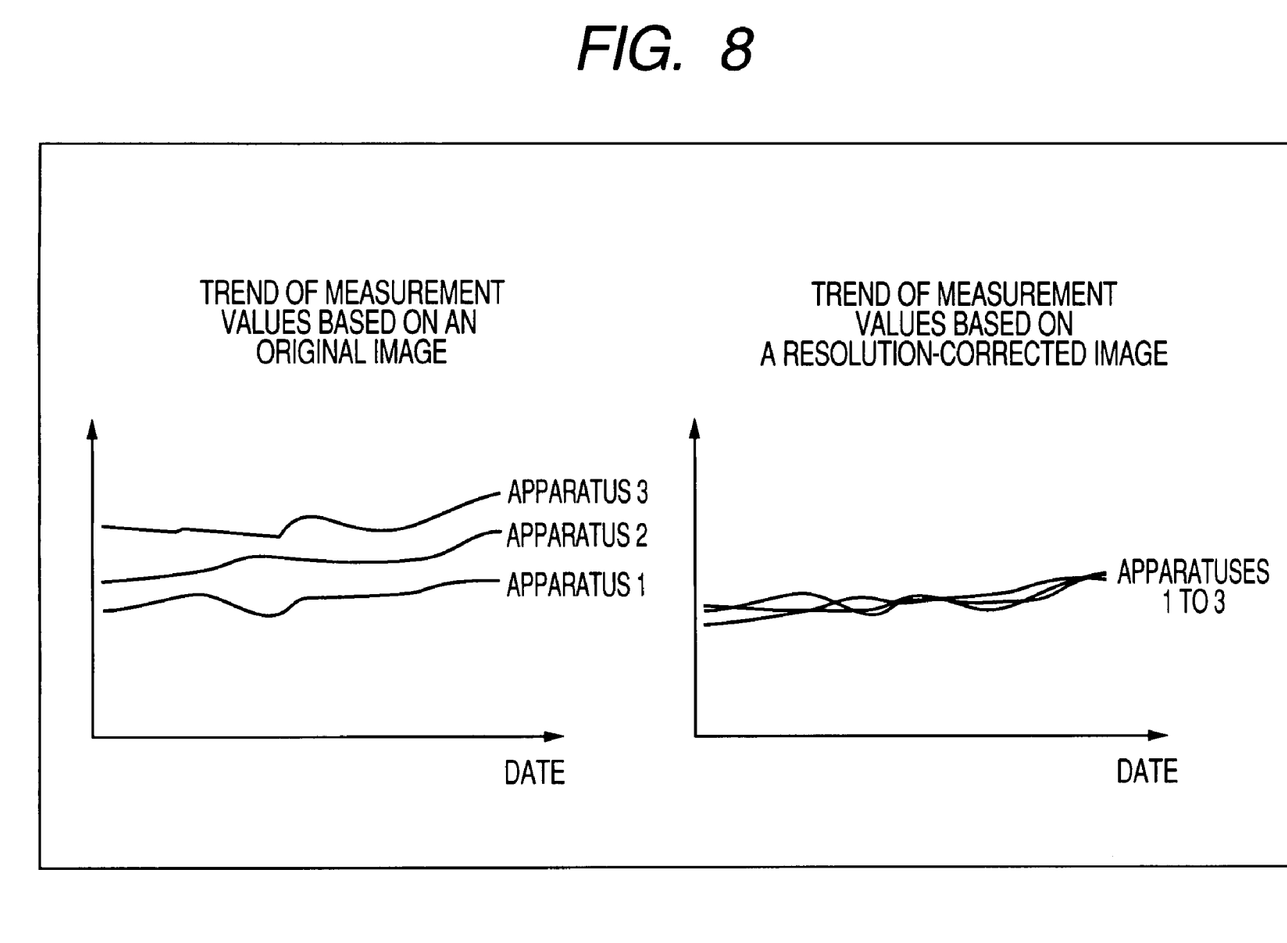
FIG. 8 is a diagram showing an embodiment of a method for displaying measurement data on a GUI window displayed on a display unit of a given electron microscope.

Next, a second embodiment of a scanning electron microscope (SEM) will be described with reference to FIGS. 6 to 8. FIG. 6 is a schematic configuration diagram showing the second embodiment of the SEM 10. This embodiment is different from the first embodiment in that a reference electron image to be acquired from a reference sample corresponding to a probe diameter during the reference time period (t=t0) is acquired from a reference sample obtained in the case where the probe diameter is subjected to a change after a given time period (t=t'), and that the main controller 400 includes a probe diameter difference detection unit (resolution difference detection unit: resolution change detection unit) 501 and an arithmetic operator generation unit 502. Of course, the probe diameter difference detection unit 501 and the arithmetic operator generation unit 502 may be included in the image processor 300, or alternatively, they may be included in the server 500 in the similar way as is the case with the first embodiment.

(1) Operation of the Second Embodiment

A case of the second embodiment wherein a reference electron image of the reference sample corresponding to the probe diameter obtained at the reference time period (t=t0) is generated from the reference electron image of the reference sample obtained in a case where the probe diameter is subjected to a change after a given time period (t=t') will be described with reference to FIGS. 6 to 8.

The flow of processes is similar to those described in the "Basic Embodiment" for the first embodiment. Further, the "Method for Detecting Difference in Probe Diameters" described for the first embodiment can be similarly applied to the second embodiment.

In advance, during the reference time period (t=t0), the reference electron image i1 (0) to be acquired from the reference sample will be acquired from the electron image acquisition unit 311 and stored in the storage device 301. (S71).

When an arithmetic operator is generated after a certain fixed time period (t=t'), the processes comprise the steps of: acquiring the reference electron image i1 (t0') to be acquired from the same reference sample by the electron image acquisition unit 311 (S72); in the probe diameter difference detection unit 501 and the arithmetic operator generation unit 502, detecting a difference in probe diameters based on the reference electron image i1 (0) during the above-stated reference time period and the reference electron image i1 (t0') after the above-stated certain fixed time period (given time period) (S73); and generating the arithmetic operator dpka or dPkb based on the difference in probe diameter thus detected (S74).

Subsequently, when measurement is made after a certain fixed time period (t=t'), the processes comprise the steps of: acquiring the measuring electron image ml (x, y) of the pattern to be measured in the electron image acquisition unit 311 (S81); and compensating and creating a compensation-measurement electron image corresponding to the probe diameter obtained during the reference time period (t=t0) by applying the arithmetic operator dPka or dPkb generated in the above to the measuring electron image ml (x, y) of the pattern to be measured that is already acquired in the above (S82). Thereafter, the measuring unit 313 executes pattern measurement by using the compensation-measurement electron image thus compensated and created (S83).

It should be noted, although the storage of images or the calculation of image processing described above may be carried out by each SEM, the data station 500 as shown in FIGS. 1 and 2 may be provided for centralized management. In the data station 500, a trend of measured values as shown in FIG. 8 may be managed.

According to the embodiment described above, it is possible to reduce a difference among measured values that are caused due to a difference in resolution that is generated as time elapses and cannot be fully adjusted in an SEM, thus enabling highly precision measurement.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An electron microscope system comprising:
a scanning electron microscope unit including:
an electron beam irradiating optical system which irradiates focused primary electron beam so as to scan to two-dimensions on a sample;
an electron image acquisition unit which acquires an electron image of the sample by detecting secondary electron and/or reflected electron that is generated from the sample irradiated the focused primary electron beam by said electron beam irradiating optical system;

an arithmetic operator processing unit which compensating the electron image of the sample acquired by the electron image acquisition unit; and a processing unit which measures dimension of a pattern formed on the sample, by processing the electron image acquired by said electron image acquisition unit and compensated by the arithmetic operator processing unit; and a data station which controls the arithmetic operator processing unit of the scanning electron microscope;

wherein, said data station further comprises:

a resolution detection unit which detects a difference between a resolution of an electron image of a reference sample pattern acquired by said electron image acquisition unit and a resolution of an electron image of the reference sample pattern acquired by another scanning electron microscope;

an arithmetic operator generation unit which generates an arithmetic operator to be applied for an electron image of a sample acquired by said scanning electron microscope unit for compensating the difference in resolution detected by said resolution detection unit; and an output unit which outputs the arithmetic operator generated by the arithmetic operator generating unit to the arithmetic operator processing unit of the scanning electron microscope unit;

wherein said arithmetic operator processing unit of the scanning electron microscope unit processes the electron image of the sample so as to compensate the difference in resolution from an electron image of the sample acquired by said another scanning electron microscope by using the arithmetic operator output from the output unit of said data station.

2. An electron microscope according to claim 1, wherein said resolution detection arithmetic operator generation unit detects a difference between a diameter of the primary electron beam of said scanning electron microscope and a diameter of a primary electron beam of said another scanning electron microscope by using the information of the resolution of said scanning electron microscope and the information of the resolution of said another scanning electron microscope that is detected from an electron image of said reference sample acquired by using said another scanning electron microscope, and said arithmetic operator generation unit generates said arithmetic operator based on said detected difference between the diameter of the primary electron beam of said scanning electron microscope and the diameter of the primary electron beam of said another scanning electron microscope.

3. An electron microscope according to claim 1, wherein said resolution detection unit calculates the resolution of the electron image of said reference sample, by calculating a brightness gradient and a local resolution in each pixel from the electron image and averaging all pixels by using the brightness gradient and the local resolution calculated.

4. An electron microscope according to claim 1, wherein said resolution detection unit calculates the resolution of the electron image of said reference sample for each orientation of the electron image.

5. An electron microscope control system comprising:

a first storage unit which stores a first electron image of a reference sample acquired by a first electron microscope;

a second storage unit which stores a second electron image of the reference sample acquired by a second electron microscope;

a resolution difference detection unit which calculates a difference in resolution between said first electron microscope and said second electron microscope by processing the first electron image of said reference sample stored in said first storage unit and the second electron image of said reference sample stored in said second storage unit;

an arithmetic operator generation unit which generates an arithmetic operator applied for an electron image that is obtained in said second microscope for compensating the difference in resolution calculated in said resolution difference detection unit; and an output unit which outputs the arithmetic operator generated in said arithmetic operator generation unit to said second electron microscope so as to enable a compensated electron image to be acquired by said second electron microscope.

6. An electron microscope control system according to claim 5, wherein said electron microscope control system is connected to said first electron microscope and said second electron microscope via a network.

7. An electron microscope control system according to claim 5, wherein the difference in resolution to be calculated in said resolution difference detection unit is a difference between a diameter of a primary electron beam of said first electron microscope which acquired the first electron image of said reference sample and a diameter of a primary electron beam of said second electron microscope which acquired the second electron image of said reference sample.

8. A method for controlling an electron microscope system comprising the steps of:

storing a first electron image of a reference sample that is acquired in a first electron microscope;

storing a second electron image of the reference sample that is acquired in a second electron microscope;

calculating a difference in resolution between said first electron microscope and said second electron microscope by processing said stored first electron image of said reference sample and said stored second electron image of said reference sample;

generating an arithmetic operator to apply for an electron image to be obtained in said second electron microscope so as to compensate for said calculated difference in the resolution; and outputting said arithmetic operator generated to said second electron microscope so as to enable obtaining a compensated electron image by said second electron microscope.

9. A method for controlling an electron microscope system according to claim 8, wherein information on said first electron image, information on said second electron image and information on said arithmetic operator generated are communicated between said first electron microscope and said second electron microscope via a network.

10. A method for controlling an electron microscope system according to claim 8, wherein the difference in resolution to be calculated is a difference between a diameter of a primary electron beam of said first electron microscope which acquired the first electron image of said reference sample and a diameter of a primary electron beam of said second electron microscope which acquired the second electron image of said reference sample.

* * * * *